United States Patent [19]

Bridges et al.

[11] Patent Number: 4,755,594

[45] Date of Patent: Jul. 5, 1988

[54] N6-SUBSTITUTED ADENOSINES

[75] Inventors: Alexander J. Bridges, Ann Arbor; Harriet W. Hamilton, Chelsea; Walter H. Moos; Deedee L. Szotek, both of Ann Arbor, all of Mich.

[73] Assignee: Warner-Lambert Company, Morris Plains, N.J.

[21] Appl. No.: 936,766

[22] Filed: Dec. 9, 1986

Related U.S. Application Data

[63] Continuation-in-part of Ser. No. 825,513, Jan. 31, 1986, abandoned.

[51] Int. Cl.[4] .................. A61K 31/70; C07H 19/167
[52] U.S. Cl. .................................. 536/26; 536/24; 536/27; 536/28; 536/29; 514/46; 514/47
[58] Field of Search .................. 514/46, 47; 536/26, 536/27, 28, 29

[56] References Cited

U.S. PATENT DOCUMENTS

| | | | |
|---|---|---|---|
| 4,590,180 | 5/1986 | Imscher et al. | 514/46 |
| 4,593,019 | 6/1986 | Bristol et al. | 514/46 |
| 4,614,732 | 9/1986 | Hamilton et al. | 514/46 |
| 4,616,003 | 10/1986 | Hamilton et al. | 514/46 |
| 4,657,897 | 4/1987 | Bristol et al. | 514/47 |
| 4,657,898 | 4/1987 | Bristol et al. | 514/47 |

Primary Examiner—Ronald W. Griffin
Assistant Examiner—L. Eric Crane
Attorney, Agent, or Firm—Joan Thierstein

[57] ABSTRACT

The present inventions are novel N6-substituted adenosines wherein the N substituent is

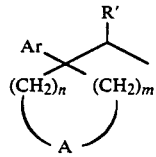

wherein Ar is an unsubstituted or substituted (1) phenyl, (2) 1- or 2-naphthalenyl, (3) 2- or 3-thienyl, (4) 2- or 3-furanyl, (5) 2-, 4-, or 5-thiazyl, (6) 2-, 3-, or 4-pyridyl, or (7) 2-pyrimidyl wherein the substituents include at least one of lower alkyl, halo, trifluoromethyl, hydroxy, lower alkoxy, lower acyloxyamino, N-lower monoalkyl or N,N-lower dialkylamino, lower thioalkyl, lower alkylsulfonyl, or nitro and R' is hydrogen or alkyl, A is

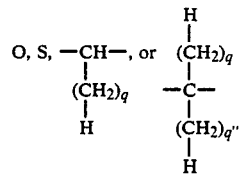

wherein q, q', or q'' are one to four, n and m are independently zero to three provided if A is a bond then n and m is at least 2 and if A is other than a bond then n and m is at least one. These novel adenosines have highly desirable central nervous system and cardiovascular activities and therefore the present invention also includes pharmaceutical compositions and methods of use therefor.

26 Claims, No Drawings

N⁶-SUBSTITUTED ADENOSINES

BACKGROUND OF THE INVENTION

This is a continuation-in-part of U.S. application Ser. No. 825,513 filed Jan. 31, 1986, now abandoned.

The novel compounds of the present invention are adenosine analogs having some of the same activities as adenosine. The compounds have a favorable ratio of affinities at $A_1$ and $A_2$ receptors and highly desirable central nervous system and cardiovascular activities, such as, analgesic, antipsychotic, sedative, antihypertensive and antianginal.

U.S. Pat. No. 3,590,029 discloses a series of 2-amino-N⁶-adenosine derivatives which may also include 2-amino-N⁶-diphenylalkyladenosines which have circulatory and cardiac activity. German publication No. 2,406,587 discloses and claims N⁶-diphenylalkyladenosines wherein the alkyl is required to be a branched chain having use as hypolipemic agents. Further, U.S. applications Ser. No. 756,922, filed July 18, 1985, now U.S. Pat. No. 4,657,898 and U.S. application Ser. No. 756,004, filed July 17, 1985, now U.S. Pat. No. 4,657,897, parent U.S. application Ser. No. 621,943, filed June 22, 1984, now abandoned which was a continuation-in-part of U.S. Ser. No. 519,284 filed Aug. 1, 1983, also now abandoned, claim N⁶-diphenylalkyladenosines wherein the alkyl is limited to straight chain moieties having highly desirable central nervous system and cardiovascular activities as now found for the novel compounds of the present invention.

SUMMARY OF THE INVENTION

The present invention relates to a compound of the formula (I)

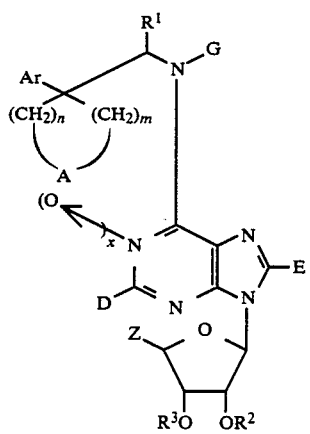

wherein

Ar is (1) phenyl, (2) 1- or 2-naphthalenyl, (3)2- or 3-thienyl, (4) 2- or 3-furanyl, (5) 2-, 4-, or 5-thiazyl, (6) 2-, 3-, or 4-pyridyl, or (7) 2-pyrimidyl wherein each of (1), (2), (3), (4), (5), (6) or (7) is unsubstituted or substituted with at least one of lower alkyl, halo, trifluoromethyl, hydroxy, lower alkoxy, lower acyloxy, amino, N-lower monoalkyl or N,N-lower dialkylamino, lower thioalkyl, lower alkylsulfonyl, or nitro;

A is a bond,

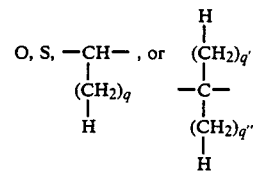

wherein q, q' or q" are independently an integer of one to four, inclusive;

n and m are independently an integer of from zero to three, inclusive, with the provision that if A is a bond then the sum of n and m must be at least two; or at least one if A is other than a bond;

$R^1$ is hydrogen or lower alkyl;

G is hydrogen, lower alkyl, benzyl, lower acyl, benzoyl;

x is an integer of zero or one;

D is hydrogen, halogen, amino, acylamino, lower alkylamino, or lower cycloalkylamino;

E is hydrogen, halogen, amino, or hydrazinyl;

Z is (1) —(CH₂)—Q wherein Q is selected from the group consisting of hydrogen, hydroxy, halogen, cyano, azido, amino, lower alkoxy, lower acyloxy, lower thioalkyl, lower sulfonylalkyl,

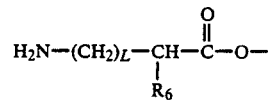

wherein L is 0–4; and $R_6$ is hydrogen or when L is 0 then $R_6$ may also be a side chain of a naturally occurring amino acid, such as, benzyl as found in a phenylalanine ester, or isopropyl as found in a valinyl ester; or

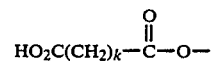

wherein k is 0–4;

—P(=Y)(OR")₂, —P(=Y)(OR")(OR'") and taken together with $R^3$ is

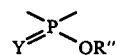

wherein Y is oxygen or sulfur and R" and R'" are independently hydrogen or lower alkyl; or (2)

wherein J is O, S, NR₇ wherein R₇ is hydrogen, lower alkyl or cycloalkyl of from 3 to 7 carbons such as cyclopropyl, cyclobutyl, cyclopentyl and the like or 1- or 2-methylcyclopropyl, 1-, or 2-ethylcyclobutyl and the like; and T is (a) NR₄R₅ wherein R₄ is straight chain lower alkyl having 1-4 carbon atoms; hydroxy, lower alkoxy or halogen substituted straight chain lower alkyl having 1-4 carbon atoms; cyclopropyl; secondary alkyl having 3-6 carbon atoms; hydroxy, lower alkoxy or halogen substituted secondary alkyl having 3-6 carbon atoms;

alkenyl having 3 to 6 carbon atoms; aralkyl having 1 to 4 carbons in the alkyl chain and optionally substituted in the aryl nucleus with hydroxy, halogen, lower alkoxy or lower alkyl groups; and heteroarylalkyl having 1 to 4 carbons in the alkyl chain and optionally substituted in the heteroaryl nucleus with hydroxy, halogen, lower alkoxy or lower alkyl groups, and $R_5$ is hydrogen, or straight chain lower alkyl having 1 to 4 carbons; or (b) $OR_4$ wherein $R_4$ is as defined above;

$R^2$ and $R^3$ are independently selected from the group consisting of hydrogen, lower alkanoyl, benzoyl, one of $R_2$ or $R_3$ is —P(=Y)(OR")$_2$ or —P(=Y)(OR")(OR'''), wherein R" and R''' are as defined above, and $R^2$ and $R^3$ are taken together to form lower alkylidene or to form

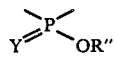

wherein Y and R" are as defined above; and pharmaceutically acceptable base salts thereof when possible or pharmaceutically acceptable acid addition salts thereof.

The present invention also relates to a pharmaceutical composition for treating diseases of the central nervous and cardiovascular system comprising an analgesic, antipsychotic, sedative, antihypertensive or antianginal effective amount of a compound having the formula I as defined above with a pharmaceutically acceptable carrier. Additionally, the instant invention is a method of treating mammals suffering from pain, psychosis, anxiety, hypertension, or angina by administering to such mammals a dosage form of a compound of the formula I as defined above.

DETAILED DESCRIPTION OF THE INVENTION

In the compounds of the formula I, the term "lower alkyl" is meant to include a straight or branched alkyl group having from 1 to 6 carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, chlorine or bromine.

Lower alkoxy and thioalkoxy are O-alkyl or S-alkyl of from 1 to 6 carbon atoms as defined above for "lower alkyl."

Lower alkanoyl is a straight or branched

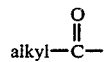

group of from 1 to 6 carbon atoms in the alkyl chain as defined above.

Lower acyloxy is

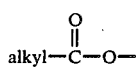

wherein alkyl is a straight or branched chain of from 1 to 6 carbon atoms as defined above.

Lower acyl is of 1 to 6 carbon atoms in a straight or branched chain alkyl group.

Lower cycloalkyl is of from 3 to 10 carbons wherein the ring is of from 3 to 7 carbons.

The compounds of formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfamate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are non-toxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine; N-benzylphenethylamine tris(hydroxymethyl)aminomethane; and the like. (See for example, "Pharmaceutical Salts," *J. Pharm. Sci.* 66(1): 1–19 (1977)).

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention may contain an asymmetric carbon atom at one of each of the two carbons connecting groups $R_1$ when $R_1$ is not hydrogen, the moiety having n and m when n is not equal to m, and Ar to the N of the amino adenosine. Thus, the invention includes the individual stereoisomers, and mixtures thereof. The individual isomers may be prepared or isolated by methods known in the art. Particularly, when Q is

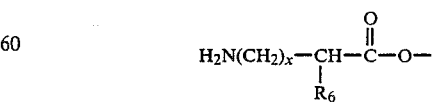

when $R_6$ is not hydrogen then the compounds of the invention include both separate enantiomers and the racemate thereof.

A preferred embodiment of the present invention includes a compound of formula I wherein G and $R^1$ are hydrogen; Ar is phenyl, 2-thienyl, or 2-furanyl (all of which may either be substituted or unsubstituted); x is zero; D and E are hydrogen; Q is hydroxy; $R^2$ and $R^3$ are hydrogen, acetyl, benzoyl or when taken together forms isopropylidene; and the sum of n and m is no more than seven.

A more preferred embodiment includes the definitions of G, $R^1$, Ar, x, D, E, Q, $R^2$ and $R^3$ for the preferred embodiment above and additionally includes the definitions A is a bond, and the sum of n and m is also limited to two or three.

Generally, the compounds of formula I may be conveniently synthesized by reacting a 6-halopurine riboside of formula II with the requisite compound of formula III which is illustrated as follows:

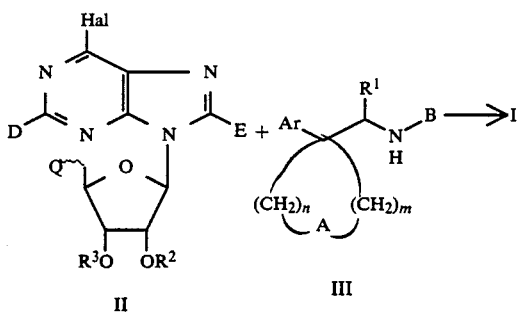

wherein Ar, $R^1$, B, n, m, A, D, E, Q, $R^3$ and $R^2$ are as defined above and Hal is halogen, preferably chlorine or bromine.

The reaction is in an inert solvent, such as alcohol, or an aprotic solvent such as dimethylformamide between from 25° to about 130° C., preferably at reflux in ethanol.

It is useful to add a base such as triethylamine, or calcium carbonate to neutralize the hydrogen halide formed as a byproduct of the reaction, but this can also be accomplished by using an extra equivalent of the compound of formula III. It is also convenient, although not necessary, to protect the ribofuranose hydroxyl groups as acetate or benzoate esters which can be removed with ammonium hydroxide or sodium methoxide following the synthesis of the $N^6$-substituted adenosines of the compounds of formula I for which it is desired to make $R^2$ and $R^3$ hydrogen.

The compound of formula II above may be one having D and E as hydrogen or halogen. The compounds of formula I wherein D and E are other than hydrogen or halogen may, thus, also be prepared in a stepwise manner from the compounds of formula I wherein D and E are halogen by replacing the halogen with D or E when each is other than halogen. This is accomplished using nucleophilic displacement conditions with a compound of the formula D—H or E—H wherein D or E is other than hydrogen or halogen. This replacement may be accomplished before removing the protective groups as discussed above.

The compounds of formula I wherein x is one can be prepared by peracid oxidation of the corresponding compounds of formula I wherein x is zero using procedures known to a skilled artisan.

Other variations in the above discussed reactions are within the skill in the art and the above discussion is thus not considered limiting.

The compounds of formula I and the pharmaceutically acceptable acid addition salts thereof are found to possess affinities for adenosine receptors (designated $A_1$ and $A_2$ receptors for convenience). These compounds are active in animal tests which are predictive of neuroleptic activity for the treatment of major psychoses such as schizophrenia. The compounds of the invention also have sedative/hypnotic properties and as such, are useful for the treatment of sleep disorders. These compounds also have analgesic properties and as such, are useful in the treatment of pain.

In addition, the compounds of the present invention are useful as antihypertensive agents for the treatment of high blood pressure. They also increase coronary blood flow and as such are useful in the treatment of angina and myocardial ischemia.

PHARMACOLOGICAL EVALUATION

Adenosine Receptor Binding—$A_1$ Receptor Affinity (RBA1)

Preparation of Membranes

Whole brain minus cerebellum and brainstem from male Long-Evans rats (150–200 g) was homogenized in 30 volumes of ice-cold 0.05M Tris-HCl buffer pH 7.7 using a Brinkman Polytron PT-10, (setting number 6 for 20 seconds) and centrifuged for ten minutes at 20,000 xg (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05M Tris-HCl buffer pH 7.7 to a concentration of 20 mg/ml original wet tissue weight and used immediately.

Assay Conditions

Tissue homogenate (10 mg/ml) was incubated in 0.05M Tris-HCl buffer pH 7.7 containing 1.0 nM [$^3$H]—$N^6$-cyclohexyladenosine ([$^3$H]—CHA) with or without test agents in triplicate for one hour at 25° C. Incubation volume was 2 ml. Unbound [$^3$H]—CHA was separated by rapid filtration under reduced pressure through Whatman glass fiber (GF/B) filters. The filters were rinsed three times with 5 ml of ice cold 0.05M Tris-HCl buffer pH 7.7. The radio-labeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occurred in the presence of 1 mM theophylline. The concentration of test agent which inhibited 50% of the specific binding ($IC_{50}$) was determined by nonlinear computer curve fit. The Scatchard plot was calculated by linear regression of the line obtained by plotting the amount of radioligand bound (pmoles/gram of tissue)

$$\text{versus} \left[ \frac{\text{bound radioligand}}{\text{free radioligand}} \right].$$

Since the amount of radioligand bound was a small fraction of the total amount added, free radioligand was defined as the concentration of (nM) of radioligand added to the incubation mixture. The Hill coefficient was calculated by linear regression of the line obtained by plotting the log of the bound radioligand vs the log of the $$\left[\frac{\text{bound radioligand}}{B_{max} - \text{bound radioligand}}\right].$$

The maximal number of binding sites ($B_{max}$) was calculated from the Scatchard plot.

Adenosine Receptor Binding—$A_2$ Receptor Affinity (RBA2)

Tissue Preparation

Brains from 200–500 g mixed sex Sprague-Dawley rats were purchased from Pel-Freez (Rogers, Ark.). Fresh brains from male Long-Evans hooded rats (Blue Spruce Farms, Altamont, NY) gave essentially identical results. Brains were thawed and then kept on ice while the striata were dissected out. Striata were disrupted in 10 vol of ice-cold 50 mM Tris.HCl (pH 7.7 at 25° C., pH 8.26 at 5° C.) (Tris) for 30 seconds in a Polytron PT-10 (Brinkmann) at setting 5. The suspension was centrifuged at 50,000 xg for ten minutes, the supernatant discarded, the pellet resuspended in 10 vol ice-cold Tris as above, recentrifuged, resuspended at 1 g/5ml, and stored in plastic vials at −70° C. (stable for at least six months). When needed, tissue was thawed at room temperature, disrupted in a Polytron, and kept on ice until used.

Incubation Conditions

All incubations were for 60 minutes at 25° C. in 12×75 mm glass tubes containing 1 ml Tris with 5 mg original tissue weight of rat weight of rat striatal membranes, 4 nM [$^3$H]—N-ethyl adenosine-5′-carboxamide ([$^3$H]NECA), 50 nM $N^6$-cyclopentyladenosine (to eliminate $A_1$ receptor binding), 10 mM $MgCl_2$, 0.1 units/ml of adenosine deaminase and 1% dimethylsulfoxide. $N^6$-Cyclopentyladenosine was dissolved at 10 mM in 0.02N HCl and diluted in Tris. Stock solutions and dilutions of $N^6$-cyclopentyladenosine could be stored at −20° C. for several months. Test compounds were dissolved at 10 mM in dimethylsulfoxide on the same day as the experiment, and diluted in dimethylsulfoxide to 100×the final incubation concentration. Control incubations received an equal volume (10 μl) of dimethylsulfoxide; the resulting concentration of dimethylsulfoxide had no effect on binding. [$^3$H]NECA was diluted to 40 nM in Tris. The membrane suspension (5 mg/0.79 ml) contained sufficient $MgCl_2$ and adenosine deaminase to give 10 mM and 0.1 units/ml, respectively, final concentration in the incubation. For test compounds with $IC_{50}$ values less than 1 μM, the order of additions was test compound (10 μl), $N^6$-cyclopentyladenosine (100 μl), [$^3$H]NECA (100 μl), and membranes (0.79 ml). For test compounds with $IC_{50}$ values greater than 1M and limited water solubility, the order of additions (same as volumes) was test compound, membranes, $N^6$-cyclopentyladenosine, and [$^3$H]NECA. After all additions, the rack of tubes was vortexed, and the tubes were then incubated for 60 min at 25° C. in a shaking water bath. The rack of tubes was vortexed an additional time halfway through the incubation.

Incubations were terminated by filtration through 2.4 cm GF/B filters under reduced pressure. Each tube was filtered as follows: the contents of the tube were poured on the filter, 4 ml of ice-cold Tris were added to the tube and the contents poured onto the filter, and the filter was washed twice with 4 ml of ice-cold Tris. The filtration was complete in about twelve seconds. Filters were put in scintillation vials, 8 ml of Formula 947 scintillation fluid added, and the vials left overnight, shaken, and counted in a liquid scintillation counter at 40% efficiency.

Data Analysis

Nonspecific binding was defined as binding in the presence of 100 μM $N^6$-cyclopentyladenosine, and specific binding was defined as total binding minus nonspecific binding. The $IC_{50}$ was calculated by weighted nonlinear least squares curve-fitting to the mass-action equation.

$$Y = T - S \cdot \frac{D}{D + K}$$

where
Y is cpm bound
T is cpm total binding without drug
S is cpm specific binding without drug
D is the concentration of drug and
K is the $IC_{50}$ of the drug Weighting factors were calculated under the assumption that the standard deviation was proportional to the predicted value of Y. Nonspecific binding was treated as a very large (infinite) concentration of drug in the computer analysis.

The $IC_{50}$ values (nM) for adenosine $A_1$ and $A_2$ receptor affinity are reported in the Table I below.

TABLE I

| Example Number | RBA-1 (nM) $IC_{50}$ | RBA-2 (nM) |
|---|---|---|
| 1 | 28 | 80 |
| 2 | 32 | 200 |
| 3 | 7.3 | 8.6 |
| 4 | 6500 | 35000 |
| 5 | 52 | 420 |
| 6 | 18 | 67 |
| 7 | 16 | 150 |
| 8 | 31 | 320 |
| 9 | 5.6 | 87 |
| 10 | 110 | 460 |
| 11 | 410 | 3200 |
| 12 | 70 | 1200 |

ANTIPSYCHOTIC EVALUATION

The compounds of the invention are new chemical substances which are useful as pharmaceutical agents for the treatment of psychoses. The antipsychotic activity of representative compounds of the invention was established by the Mouse Activity and Screen Test Procedure (MAST) described below.

Animals

Nine unfasted Swiss-Webster male mice weighing 20–30 g are equally divided into three groups for each drug dose to be tested. That is, data for each dose level was generated by three separate groups of three mice each.

Drugs

A minimum of three dose levels (10, 30, and 100 mg/kg) are tested for each drug. Treatments are administered intraperitoneally one hour prior to testing. All dosages are calculated as parent compound and given in volumes of 10 ml/kg. Compounds are dissolved or suspended in 0.2% Methocel. Control animals are injected with Methocel.

Testing

A two part testing procedure is started one hour postinjection. First, the screen test (ST) is performed (see *Pharmac. Biochem. Behav.* 6, 351-353, 1977). Briefly this test consists of placing mice on individual wire screens which are then rotated 180 degrees at the start of a 60 second observation period. The number of mice falling off the inverted screen is recorded.

Immediately following the screen test, the final phase of testing is initiated by placing each group of three mice in one actophotometer (*Life Sciences*, 22, 1067-1076, 1978). The actophotometer consists of a cylindrical chamber whose center is occupied by another cylinder which contains the illumination for six photocells located on the perimeter of the chamber. Six light-beam interruptions equal one count. Locomotor activity is recorded by computer at ten minute intervals for 60 minutes.

Data

The data obtained from the screen test are expressed as percent of mice falling off the screen. Data derived from locomotor activity of drug treated mice are compared to the activity of vehicle treated animals and are expressed as percent inhibition of spontaneous locomotion. All percentages reported for inhibition of locomotion (LI) are based upon data accumulated for one hour. Both phases of testing are graded: A=60-100%; C=31-59%; and N=0-30%. An overall dose rating is obtained by the following criteria:

| Inhibition of Locomotion Rating | with | Screen Test Failure Rating | = | Dose Rating |
|---|---|---|---|---|
| A | — | N or C | = | A |
| A | — | A | = | C |
| C | — | N or C | = | C |
| All other combinations | | | = | N |

LAD refers to the lowest dose at which an A rating is achieved. Compounds which exhibit an overall dose rating of A at a dose of 100 milligrams/kilogram or less are considered active. Utilizing this procedure, an overall dose rating of A was obtained for the noted compound in Table II at the indicated dose. The compounds are idendified in the Examples.

TABLE II

| Example | Dose (IP) | Inhibition of motor activity (%) | Inhibition of screen test failure (%) |
|---|---|---|---|
| 1 | .05 | | |
| | 0.3 | 43 | 11 |
| | 1.0 | 48 | 0 |
| | 3.0 | 38 | 0 |
| | 10 | 92 | 0 |
| | 30 | 98 | 22 |
| | 100 | 100 | 44 |
| 2 | 3 | 19 | 11 |
| | 10 | 69 | 0 |
| | 30 | 90 | 0 |
| 3 | 0.03 | 17 | 0 |
| | 0.1 | 40 | 0 |
| | 0.3 | 70 | 0 |
| | 1.0 | 85 | 0 |
| | 3.0 | 89 | 0 |
| | 10 | 93 | 0 |
| 4 | (RAT orally (PO)) | | |
| | 1 | 2 | 11 |
| | 3 | 15 | 0 |
| | 10 | 2 | 0 |
| 5 | 3 | 16 | 11 |
| | 10 | 10 | 0 |
| | 30 | −4 | 0 |
| 6 | 3 | 11 | 0 |

TABLE II-continued

| Example | Dose (IP) | Inhibition of motor activity (%) | Inhibition of screen test failure (%) |
|---|---|---|---|
| | 10 | 16 | 0 |
| | 30 | 51 | 0 |
| 7 | 1.0 | 5 | 0 |
| | 3.0 | 21 | 0 |
| | 10.0 | 82 | 0 |
| 8 | 3 | 22 | 0 |
| | 10 | 35 | 0 |
| | 30 | 73 | 0 |
| 9 | 3 | 43 | 0 |
| | 10 | 86 | 0 |
| | 30 | 94 | 0 |
| 10 | 3 | −7 | 11 |
| | 10 | 12 | 0 |
| | 30 | 49 | 22 |
| 11 | 3 | 15 | 11 |
| | 10 | −10 | 0 |
| | 30 | 34 | 0 |
| 12 | 3 | −4 | 0 |
| | 10 | 5 | 0 |
| | 30 | 20 | 0 |

Representative compounds of the invention (identified in the Examples) were also tested for antipsychotic activity according to the following protocol (SIDR or SIDSM). The noted compound has the indicated $ED_{50}$ values (mg/kg) and is considered active as an antipsychotic agent in the test procedure.

Procedure

Mature male Long-Evans rats (SIDR) or squirrel-monkeys (SIDSM) are conditioned to push a lever in order to avoid a painful electric footshock. If the animals fails to push the lever, he receives a shock every ten seconds until the lever is pushed. Shocks can be terminated by pushing the lever. Thereafter, as long as the lever is pushed at least once every 20 seconds, there will be no shock.

Each animal acts as its own control; one weekly session is used to establish baseline behavior and another session later in the week is used as a drug session. Once patterns of avoidance are established, the effects of standard and unknown compounds are studied.

When tested by the above procedure representative compound of Example 1 as shown hereinafter shows an $ED_{50}$ in the SIDR protocol (that is in the rat) as described above of 0.55 mg/kg and in the SIDSM (that is in the squirrel-monkey) as described above of 0.52 mg/kg.

RESPONSE EVALUATION

All events are electronically programmed and the response to these events counted or used as feed-back to the program.

ANTIHYPERTENSIVE EVALUATION (AHP3)

The usefulness of the compounds of the present invention as antihypertensive agents is demonstrated by their effectiveness in standard pharmacological test procedures, for example, in causing a significant decrease in mean arterial blood pressure in the conscious rat. This test procedure is described in the following paragraphs.

A Method for the Direct Monitoring of Aortic Blood Pressure and Heart Rate from Conscious Rats The continuous monitoring of pulsatile blood pressure (BP) from unrestrained conscious rats surgically equipped with polyethylene cannulas was accomplished by means of a computer assisted data capture scheme (CADCS). The basic elements of the methodology are the cannulation procedure and the CADCS.

Method

Cannulation Procedure

Rats were anesthetized with Telazol (1:1 tiletamine HCl and zolazepam HCl); 20–40 mg/kg IM and the descending aorta exposed via a midline incision. Cannulas fabricated from polyethylene tubing were inserted into the aorta via an undersized puncture hole below the renal arteries. The puncture hole was made by a 23 G disposable needle with a section of the aorta clamped off above and below the puncture site. The cannulas, consisting of a PE100 (0.86 mm ID) body and a PE50 (0.58 mm ID) tip, were attached to a trocar, inserted through the psoas muscle, and passed subcutaneously along the midline of the back and externalized between the ears. The cannulas were anchored to the psoas muscle and between the scalulae (3-0 green braided suture). The midline incision was closed in two steps (muscle first, skin second) using continuous over-and-over sutures (4-0 chronic). Each rat was then given penicillin 30,000 units subcutaneously (Penicillin G Procaine Sterile Suspension).

The rats were fitted with a harness-spring-swivel assembly designed to protect the cannula and to provide the rat relative freedom of movement. The harnesses were fabricated from nylon hook and loop tape cemented to a metal plate to which spring wires (18-8 stainless steel) were attached to brass swivels. Each polyethylene cannula was channeled through a spring and connected through a swivel to a pressure transducer (Model P23Gb; Statham Instruments; Hato Rey, Puerto Rico) and an infusion pump (Sage model 234-7; Orion Research, Cambridge MA) by means of PE100 tubing. While on test, each rat received a continuous slow infusion of heparinized saline solution (approximately 400 μl or 40 units of heparin per 24 hours period) to prevent clot formation. Additional "flushes" of the cannula with heparinized saline were carried out when the aortic pulse pressure (systolic minus diastolic) was less than 25 mm Hg.

CADCS

The pulsatile blood pressure and heart rate of each of 32 rats was monitored every minute by means of two in-laboratory microcomputers communicating directly with a data concentrator computer. The data were first stored on the data concentrator disk and then transferred to a magnetic tape for analysis and report generation by the main research computer. The overall scheme involved modulating the primary signal from the pressure transducer, generating the primary data set of the one-minute values for systolic, diastolic, and mean blood pressures and heart rate by the in-lab microcomputer and the storage, analysis, and report generation by the main research computer.

The transducers were connected to analog signal conditioning modules. The modules provided a regulated excitation voltage for the transducers, amplification as required to interface the microprocessors and an active low pass filter to compensate for the pressure wave form distortion produced by the flexible, fluid filled, narrow cannula. The distortion was 22–26 Hz and this provided a reliable estimate of both systolic and diastolic blood pressure.

The microcomputers (one for each of two groups of 16 rats) were connected to the input components through the module interface units, an analog-to-digital converter for the pressure wave form signal and the digital inputs for the dose and event marker switches. The microcomputer controlled the sequential acquisition of data from the modular interface units through an internal synchronous time-of-day clock/time base generator. Utilizing the time base generator as a reference, the blood pressure values and the marker switch status for each of the 32 stations were sampled every ten msec. The microcomputer processed each blood pressure sample as it was received to produce "running average" values for heart rate, and mean, systolic and diastolic blood pressure.

When tested by the above procedure, compounds of the Examples as noted produced the following changes in MAP (mean arterial pressure) and heart rate.

TABLE III

| Example Number | Dose Mg/Kg | Maximum BP ↓ MAP |
|---|---|---|
| 1 | 1 | 13% |
|   | 3 | 23% |
|   | 10 | 23% |
| 3 | 3 | 43% |
| 7 | 10 | 32% |
| 9 | 3 | 10% |
| 10 | 10 | 10% |
| 11 | 10 | 5% |
| 12 | 10 | 23% |

LAD refers to the lowest dose tested at which a 10% reduction in blood pressure for four consecutive hours is achieved.

Accordingly, the present invention also includes a pharmaceutical composition for treating psychoses, sleep disorders, pain, hypertension or angina comprising a corresponding antipsychotic, sedative, analgesic, antihypertensive or antianginal effective amount of a compound of the formula I as defined above together with a pharmaceutically acceptable carrier.

The present invention further includes a method for treating psychoses, sleep disorders, pain, hypertension, or angina in mammals suffering therefrom comprising administering to such mammals either orally or parenterally a corresponding pharmaceutical composition containing a compound of the formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substance which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium sterate, talc, sugar, lactose, pectin, dextrin, starch, gellatin, tragacanth, methylcellulose, sodium carboxymethylcellulose, a low melting wax, cocoa butter, and the like. The term "preparation" is intended to include the formulation of the active compound with encapsulating material as carrier providing a casule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself or it can be the appropriate number of any of these in packaged form.

The quantity of active compound in a unit dose of preparation may be varied or adjusted from 0.01 mg 500 mg preferably to 0.1 to 50 mg according to the particular application and the potency of the active ingredient. The compositions can, if desired, also contain other compatible therapeutic agents.

In therapeutic use as described above, the mammalian dosage range for a 70 kg subject is from 0.01 to 150 mg/kg of body weight per day or preferably 0.5 to 50 mg/kg of body weight per day. The dosages, however, may be varied depending upon the requirements of the patient, the severity of the condition being treated, and the compound being employed.

Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention, but are not meant to be limiting thereto.

EXAMPLE 1

N6-((1-Phenylcyclopropyl)methyl)adenosine

A mixture of 6-chloropurine riboside (8.61 g, 30 mmol), (1-phenylcyclopropyl)methylamine (4.41 g, 30 mmol) and triethylamine (6.06 g, 60 mmol) are refluxed in stirring ethanol (300 mL) under $N_2$ for 20 h. On cooling to 0° the product crystallized. Vacuum filtration and drying in vacuo gives N6-((1-phenylcyclopropyl)methyl)adenosine (9.24 g, 79%) as a very pale khaki solid m.p. 118°–23° C. Found: C, 59.58; H, 5.77; N, 17.49%. $C_{20}H_{23}N_5O_4$ calculated requires: C, 60.45; H, 5.79; N, 17.63%.

(1-Phenylcyclopropyl)methylamine

Phenylacetonitrile (5.85 g, 50 mmol) in DMSO (dimethylsulfoxide) (20 mL) is added dropwise over 45 min to a slurry of oil-free NaH (3.0 g, 125 mmol) in stirred DMSO (100 mL) at 25° under $N_2$. Vigorous gas evolution occurs. After a further 30 min 1,2-dibromoethane (14.1 g, 75 mmol) in DMSO (20 mL) is added dropwise over 1 h. The reaction mixture turns purple, heats up to about 50°, and further gas evolution occurs. After a further 1 h the reaction mixture is poured slowly onto ice water (250 mL, gas evolution), and is extracted with ether (3×50 mL). The combined extracts are washed with water (2×100 mL) and saturated brine (100 mL) and dried (MgSO4). The solvent is removed under reduced pressure to give 1-phenylcyclopropane carbonitrile (6.58 g, 92%) as a mobile brown oil. Nmr δ (CDCl3) 7.25–7.40 (5H, m), 1.6–1.8, 1.2–1.45 (2H and 2H, AA'BB').

LiAlH4 (1.8 g, 48 mmol) is added in batches over 5 min to a solution of 1-phenylcyclopropane carbonitrile (6.58 g, 46 mmol) in ether (200 mL) stirred under $N_2$ at 0°. After 1 h the reaction mixture is quenched by a careful dropwise addition of water (1.8 mL), 10% W/V NaOH solution (1.8 mL) and water (5.4 mL). Vigorous gas evolution again occurs. The mixture is vacuum filtered, and the filtrate is extracted with dilute HCl (0.2M, 3×100 mL). The combined extracts are washed with ether (3×100 mL) and made basic with NaOH pellets (3.2 g, 80 mmol). The aqueous layer is extracted with ether (3×100 mL). The combined organic phases are washed with water (2×100 mL), saturated brine (100 mL) and dried (MgSO$_4$). The solvent is removed under reduced pressure to give (1-phenylcyclopropyl)methylamine (4.98 g, 74%) as an orange oil. Nmr δ (CDCl$_3$) 7.1–7.5 (5H, m), 2.77 (2H, S), 1.3 (2H, br s), 0.6–0.95 (4H, m).

EXAMPLE 2

N6-((1-(3-Chlorophenyl)cyclopropyl)methyl)adenosine (1-(3-Chlorophenyl)cyclopropyl)methylamine is prepared from (3-chlorophenyl)acetonitrile as described in Example 1.

Reaction of the above amine (1.82 g, 10 mmol) with 6-chloropurine riboside (2.87 g, 10 mmol) and triethylamine (2.02 g, 20 mmol) as described in Example 1 gives, N6-((1-(3-chlorophenyl)cyclopropyl)methyl)adenosine (3.42 g, 79%) as an off-white crystalline solid m.p. 71°–95°, in 74% overall yield. Found: C, 55.30; H, 5.05; N, 16.30; Cl, 8.15%. C$_{20}$H$_{22}$N$_5$O$_4$Cl calculated requires: C, 55.62; H, 5.10; N, 16.22; Cl, 8.23%.

EXAMPLE 3

N6-((1-Thien-2-ylcyclopropyl)methyl)adenosine (1-Thien-2-ylcyclopropyl)methylamine is prepared from 2-thienyl acetonitrile and 1,2-dibromoethane as described in Example 1 in 57% overall yield.

Reaction of the above amine (1.53 g, 10 mmol) with 6-chloropurine riboside (2.87 g, 10 mmol) and triethylamine (2.02 g, 20 mmol) as described in Example 1 gives, after a second crystallization from ethanol, N6((1-thien-2-ylcyclopropyl)methyl)adenosine (2.90 g, 71%) as a fluffy off-white solid m.p. 136°–138.5° C. Found: C, 53.78; H, 5.45; N, 17.28; S, 7.52%. C$_{18}$H$_{21}$N$_5$O$_4$S calculated requires: C, 53.60; H, 5.21; N, 17.37; S, 7.94%.

EXAMPLE 4

N6-((1-Phenylcyclopropyl)methyl)adenosine-N1-oxide m-Chloroperoxybenzoic acid (1.80 g, 85%, 9 mmol) and BHT stabilizer (0.20 g) in THF (10 mL) are added over 30 min to a solution of N6((1-phenylcyclopropyl)methyl)adenosine (1.19 g, 3 mmol), in refluxing tetrahydrofuran (THF) (5 mL). After a further 30 min the solvent is removed under reduced pressure, and the residue is purified by flash chromatography on silica gel, eluting with 7.5% then 15% CH$_3$OH in CHCl$_3$, then by preparative tlc on silica gel eluting once with 10% CH$_3$OH in CHCl$_3$. The major band r.f. 0.38 is extracted with CHCl$_3$/CH$_3$OH, and the solvent is removed rigorously under reduced pressure to give N6(1-phenylcyclopropyl)methyl)adenosine-N,1-oxide (0.48 g, 39%) as a white solid foam m.p. 105°–113° C. Found: C, 57.01, H, 5.55; N, 16.51%. C$_{20}$H$_{23}$N$_5$O$_5$ calculated requires: C, 58.11; H, 5.57; N, 16.95%. IR 1647, 1579, 1502, 1214 cm$^{-1}$.

EXAMPLE 5

5'-Deoxy-5'-chloro-N6-((1-phenylcyclopropyl)methyl)adenosine

A solution of (1-phenylcyclopropyl)methylamine (0.55 g, 3.75 mmol), prepared as in Example 1, 6-chloropurine-5'-deoxy-5'-chlororiboside-2',3'-isopropylidene (1.25 g, 3.6 mmol) and triethylamine (0.75 g, 7.5 mmol) is refluxed in ethanol (40 ml) under N$_2$ for 24 h. The solvent is removed under reduced pressure and the brown gummy residue is partitioned between ethyl acetate (50 mL) and water (25 mL). The organic phase decanted and washed with water (25 mL), saturated brine (25 mL) and dried (MgSO$_4$). The solvent is removed under reduced pressure and the residual light brown oil is heated under N$_2$ in aqueous formic acid (50%, 20 mL) for 4 h. The solvent is removed under reduced pressure, and the residual light brown oil is heated under N$_2$ in aqueous formic acid (50%, 20 mL) for 4 h. The solvent is removed under reduced pressure, and the residue is dissolved in ethyl acetate (50 mL) and is washed with saturated NaHCO$_3$ solution (25 mL), water (25 mL), saturated brine (25 mL) and dried (MgSO$_4$). The solvent is removed under reduced pressure and the residual brown gummy foam is purified by preparative tlc on silica gel, eluting once with 10% CH$_3$OH in CHCl$_3$. The major band, r.f. 0.41, is extracted with CHCl$_3$/MeOH, and the solvent is removed rigorously under reduced pressure to give 5'-deoxy-5'-chloro-N6-((1-phenylcyclopropyl)methyl)adenosine (0.40 g, 27%) as a pale khaki solid foam m.p. 73°–8° C. Found: C, 56.74; H, 5.20; N, 16.80; Cl, 9.13%. C$_{20}$H$_{22}$ClN$_5$O$_3$ calculated requires: C, 57.76; H, 5.29; N, 16.85; Cl, 8.54%.

6-Chloropurine-5'-deoxy-5'-chlororiboside-2',3'-isopropylidene

Phosphorus oxychloride (12.28 g, 80 mmol) is added dropwise over 5 min to a stirred mixture of inosine-2',3'-isopropylidene (6.16 g, 20 mmol), tetraethylammonium chloride (6.60 g, 40 mmol), N,N-dimethylaniline (9.6 g, 80 mmol), and freshly powdered calcium hydride (0.52 g, 20 mmol) in acetonitrile (40 mL) under N$_2$ at 25°. After another 5 minutes the mixture is refluxed for 15 min. On cooling the volatiles are removed under reduced pressure, and the residual oil is diluted with CHCl$_3$ (200 mL) and poured onto a vigorously stirred mixture of 50% saturated Na$_2$CO$_3$ soln (500 mL) and ice (250 mL). The organic phase is separated, and the aqueous phase is extracted with CHCl$_3$ (2×50 mL). The combined organic extracts are washed with saturated sodium carbonate solution (100 mL), and dried (Na$_2$SO$_4$). The solvent is removed under reduced pressure and the residual oil is purified by chromatography on silica gel eluting with CHCl$_3$, 2 then 4% CH$_3$OH in CHCl$_3$. The solvent is removed under reduced pressure to give 6-chloropurine-5'-deoxy-5'-chlororiboside-2',3'-isopropylidene (2.50 g, 36%) as an orange-brown gum. Nmr (CDCl$_3$) δ8.67 (1H, s), 8.25 (1H, s), 6.15 (1H, d, J=2.5 Hz), 5.33, 5.03 (1H and 1H, ABq of d, J$_{AB}$=6 Hz, J$_d$=2.5, 3 Hz), 4.46 (1H, d of t, J$_d$=3 Hz, J$_t$=6 Hz), 3.5–3.85 (2H, ABq of d, J$_{AB}$=12 Hz, J$_d$=6 Hz), 1.65 (3H, s), 1.41 (3H, s).

EXAMPLE 6

5'-Chloro-5'-deoxy-N6-((1-thien-2-ylcyclopropyl)methyl)adenosine (1-Thien-2-ylcyclopropyl)methylamine (0.55 g, 3.6 mmol), see Example 3, 6-chloropurine-5'-deoxy-5'-chlororiboside-2',3'-isopropylidene (1.25 g, 3.6 mmol, as prepared in Example 5) and triethylamine (0.75 g, 7.5 mmol) are reacted together as described in Example 5. Aqueous formic acid hydrolysis gives 5'-chloro-5'-deoxy-N6-((1-thien-2-ylcyclopropyl)methyl)adenosine (0.44 g, 29%) as a light khaki solid foam m.p. 69°–75° C. Found: C, 50.53; H, 4.90; N, 15.90; Cl, 9.13; S, 7.22%. C$_{18}$H$_{20}$ClN$_5$O$_3$S calculated requires: C, 51.25; H, 4.74; N, 16.61; Cl, 8.42; S, 7.59%.

EXAMPLE 7

N6-((1-Phenylcyclobutyl)methyl)adenosine (1-Phenylcyclobutyl)methylamine is prepared from phenylacetonitrile (2.93 g, 25 mmol) and 1,3-dibromopropane (7.57 g, 37.5 mmol) as described in Example 1 in 62% yield. The above amine (1.61 g, 10 mmol) is reacted with 6-chloropurine riboside (2.87 g, 10 mmol) as described in Example 1. As the compound did not crystallize it is purified by removal of the solvent under reduced pressure, followed by dissolving the residual gum in ethyl acetate (50 mL) and washing it with water (2×25 mL) and saturated brine (25 mL) and drying ($MgSO_4$). The solvent is removed under reduced pressure and the residual gum is subjected to flash chromatography on silica gel, eluting with 5% $CH_3OH$ in $CHCl_3$. N6-((1-phenylcyclobutyl)methyl)adenosine (2.40 g, 58%) is obtained as a white solid foam m.p. 95°–118° C. Found: C, 61.21; H, 6.23; N, 17.24%. $C_{21}H_{25}N_5O_4$ calculated requires: C, 61.31; H, 6.08; N, 17.03%.

EXAMPLE 8

N6-((1-(3-Chlorophenyl)cyclobutyl)methyl)adenosine (1-(3-Chlorophenyl)cyclobutyl)methylamine is prepared from (3-chlorophenyl)acetonitrile (3.79 g, 25 mmol) and 1,3-dibromopropane (7.57 g, 375 mmol) as described in Example 1 in 60% overall yield.

The above amine (1.96 g, 10 mmol) is reacted with 6-chloropurine riboside (2.87 g, 10 mmol) and purified as described in Examples 1 and 7 above. N6-((1-(3-chlorophenyl)cyclobutyl)methyl)adenosine (3.66 g, 82%) as a pale yellow solid foam is obtained m.p. 92°–8° C. Found: C, 56.11; H, 5.33; N, 15.44; Cl, 8.99%. $C_{21}H_{24}ClN_5O_4$ calculated requires: C, 56.57; H, 5.39; N, 15.71; Cl, 7.97%.

EXAMPLE 9

N6-((1-Thien-2-ylcyclobutyl)methyl)adenosine (1-Thien-2-ylcyclobutyl)methylamine is prepared from thien-2-ylacetonitrile (3.70 g, 30 mmol), 1,3-dibromopropane (9.09 g, 45 mmol), as described in Example 1 in 55% yield.

The above amine (1.67 g, 10 mmol) is reacted with 6-chloropurine riboside (2.87 g, 10 mmol) as described in Example 1 and 7 is purified by column chromatography to give N6-(1-(thien-2-ylcyclobutyl)methyl)adenosine (3.18 g, 76%) as a colorless glass m.p. 84°–92° C. Found: C, 54.88; H, 5.69; N, 16.77; S, 7.55%. $C_{19}H_{23}N_5O_4S$ calculated requires: C, 54.68; H, 5.52; N, 16.79; S, 7.67%.

EXAMPLE 10

N6-((1-Phenylcyclopentyl)methyl)adenosine (1-Phenylcyclopentyl)methylamine is prepared as its hydrochloride salt, m.p. 185°–6° C. from 1-phenylcyclopentane carbonitrile as described in Example 11.

The above amine hydrochloride (5.0 g, 24 mmol) is reacted with 6-chloropurine riboside (6.8 g, 24 mmol) as described in Example 11 infra to give after column chromatography N6-((1-phenylcyclopentyl)methyl)adenosine (3.80 g, 37%) as a solid white foam m.p. 74°–8° C. Found: C, 59.02; H, 5.94; N, 15.25%. $C_{22}H_{27}N_5O_4$ calculated requires: C, 62.12; H, 6.35; N, 16.47%. $C_{22}H_{27}N_5O_4$ 0.25 $CHCl_3$ requires C, 58.69; H, 6.03; N, 15.38%.

EXAMPLE 11

N6-((1-Phenylcyclohexyl)methyl)adenosine (1-Phenylcyclohexyl)methylamine (1.80 g, 8 mmol) as prepared below, and 6-chloropurine riboside (2.36 g, 8 mmol) are reacted as described in Example 1. The solvent is removed under reduced pressure, and the residue dissolved up in $CHCl_3$ and washed with water and dried ($MgSO_4$). The solvent is removed under reduced pressure and the residual white foam is purified on silica gel chromatography eluting with 10% MeOH in $CH_2Cl_2$ to give N6-((1-phenylcyclohexyl)methyl)adenosine (1.49 g, 42%) as a white glass m.p. 87°–9° C. Found: C, 62.22; H, 6.96; N, 15.70%. $C_{23}H_{29}N_5O_4$ calculated requires: C, 62.87; H, 6.61; N, 15.95%.

(1-Phenylcyclohexyl)methylamine

1-Phenylcyclohexane carbonitrile is reduced with $H_2$ in methanol containing 16% ammonia with a Raney nickel catalyst. The catalyst is filtered off and (1-phenylcyclohexyl)methylamine is precipitated as its hydrochloride salt m.p. 230°–33° C., by treatment with methanolic HCl and isopropyl ether.

EXAMPLE 12

N6-((1-(4-Chlorophenyl)cyclopropyl)methyl)adenosine (1-(4-Chlorophenyl)cyclopropyl)methylamine is prepared from 4-chlorophenyl acetonitrile and ethylene dibromide in overall 33% yield as described in Example 1.

Reaction of the above amine (1.48 g, 8 mmol) with 6-chloropurine riboside (2.09 g, 7.3 mmol) and triethylamine (1.1 mL, 8 mmol) as prepared in Example 1 and 7 gives N6-((1-(4-chlorophenyl)cyclopropyl)methyl)adenosine (1.47 g, 47%) as a cream colored solid m.p. 132°–8° C. Found: C, 56.16; H, 5.22; N, 15.54; Cl, 9.12%. $C_{20}H_{22}N_5O_4Cl$ calculated requires: C, 55.62; H, 5.10; N, 16.22; Cl, 8.23%.

Also made by a process analogous to Example 1 were,

EXAMPLE 13
N6-(1-(4-Methoxyphenyl)cyclopropylmethyladenosine m.p. 88°-91° C.;

EXAMPLE 14
N6-(1-(3,4-Dichlorophenyl)cyclopropylmethyl)adenosine m.p. 120°-22° C.;

EXAMPLE 15
N6-(1-(2-methoxyphenyl)cyclopropylmethyl)adenosine m.p. 82°-90° C.;

EXAMPLE 16
N6-(1-Thien-3-yl)cyclopropylmethyl)adenosine m.p. 122°-7° C.;

EXAMPLE 17
N6-(1-(5-Bromothien-2-yl)cyclopropylmethyl)adenosine m.p. 112°-8° C.;

EXAMPLE 18
N6-(1-Naphth-2-ylcyclopropylmethyladenosine m.p. 91°-5° C.;

EXAMPLE 19
N6-(1-Naphth-2-ylcyclobutylmethyladenosine m.p. 110°-8° C.;

EXAMPLE 20
N6-(1-(2-Chlorophenyl)cyclopropylmethyl)adenosine m.p. 93°-101° C.

EXAMPLE 21
N6-(1-(2-Methylphenyl)cyclopropylmethyl)adenosine m.p. 95°-99° C.

EXAMPLE 22
N6-(1-(2-Furanyl)cyclopropylmethyl)adenosine m.p. 128°-30° C.

EXAMPLE 23
N6-(1-(5-Methylthien-2-yl)cyclopropylmethyl)adenosine m.p. 103°-106° C.

EXAMPLE 24
N6-(1-phenylcyclopropylmethyl)adenosin-5$^1$-yl hydrogen succinate m.p. 143°-5° C.

EXAMPLE 25
N6-(1-phenylcyclopropylmethyl)adenosine-5$^1$-uronamide m.p. 203°-5° C.

We claim:
1. A compound of the formula

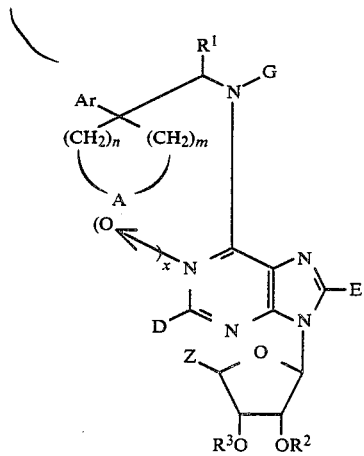

wherein
Ar is (1) phenyl, (2) 1- or 2-naphthalenyl, (3) 2- or 3-thienyl, (4) 2- or 3-furanyl, (5) 2-, 4-, or 5-thiazolo, (6) 2-, 3-, or 4-pyridyl, or (7) 2-pyrimidyl wherein each of (1), (2), (3), (4), (5), (6) or (7) is unsubstituted or substituted with at least one of lower alkyl, halo, trifluoromethyl, hydroxy, lower alkoxy, lower acyloxy, amino, N-lower monoalkyl or N,N-lower dialkylamino, lower thioalkyl, lower alkylsulfonyl, or nitro;

E is hydrogen, halogen, amino, or hydrazine;

A is a bond,

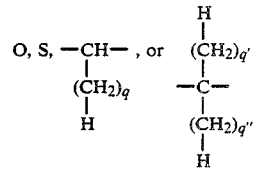

wherein q, q' or q'' are independently an integer of one to four, inclusive;

n and m are independently an integer of from zero to three, inclusive, with the provision that if A is a bond then the sum of n and m must be at least two; or at least one if A is other than a bond;

$R^1$ is hydrogen or lower alkyl;

G is hydrogen, lower alkyl, benzyl, lower acyl, benzoyl;

x is an integer of zero or one;

D is hydrogen, halogen, amino, acylamino, lower alkylamino, or lower cycloalkylamino;

E is hydrogen, halogen, amino, or hydrazinyl;

Z is (1) —(CH$_2$)—Q wherein Q is selected from the group consisting of hydrogen, hydroxy, halogen, cyano, azido, amino, lower alkoxy, lower acyloxy, lower thioalkyl, lower sulfonylalkyl,

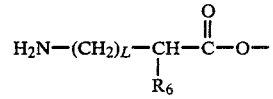

wherein L is 0–4; and $R_6$ is hydrogen or when L is 0 then $R_6$ may also be a side chain of a naturally occurring amino acid, or

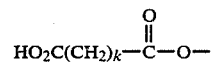

wherein k is 0–4;

—P(=Y)(OR'')$_2$, —P(=Y)(OR'')(OR''') and taken together with $R^3$ is

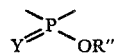

wherein Y is oxygen or sulfur and R'' and R''' are independently hydrogen or lower alkyl; or (2)

wherein J is O, S, NR$_7$ wherein R$_7$ is hydrogen, lower alkyl or cycloalkyl of from 3 to 7 carbons and T is (a) NR₄R₅ wherein R₄ is straight chain lower alkyl having 1–4 carbon atoms; hydroxy, lower alkoxy or halogen substituted straight chain lower alkyl having 1–4 carbon atoms; cyclopropyl; secondary alkyl having 3–6 carbon atoms; hydroxy, lower alkoxy or halogen substituted secondary alkyl having 3–6 carbon atoms; alkenyl having 3 to 6 carbon atoms; aralkyl having 1 to 4 carbons in the alkyl chain unsubstituted and substituted in the aryl nucleus with hydroxy, halogen, lower alkoxy or lower alkyl groups; and heteroarylalkyl having 1 to 4 carbons in the alkyl chain unsubstituted and substituted in the heteroaryl nucleus with hydroxy, halogen, lower alkoxy or lower alkyl groups, and R₅ is hydrogen, or straight chain lower alkyl having 1 to 4 carbons;

or (b) OR₄ wherein R₄ is as defined above;

R² and R³ are independently selected from the group consisting of hydrogen, lower alkanoyl, benzoyl, one of R₂ or R₃ is —P(=Y)(OR")₂ or —P(=Y)(OR")(OR'''), wherein R" and R''' are as defined above, and R² and R³ are taken together to form lower alkylidene or to form

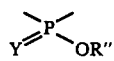

wherein Y and R" are as defined above; and pharmaceutically acceptable base salts thereof or pharmaceutically acceptable acid addition salts thereof.

2. A compound of claim 1, wherein x is 0.

3. A compound of claim 2 wherein Ar is phenyl unsubstituted or substituted with at least one of lower alkyl, halo, trifluoromethyl, hydroxy, lower alkoxy, lower acyloxy, amino, N-lower monoalkyl or N,N-lower dialkylamino, lower thioalkyl, lower alkylsulfonyl, or nitro; 2-thienyl unsubstituted or substituted with at least one of lower alkyl, halo, trifluoromethyl, hydroxy, lower alkoxy, lower alyloxy, amino, N-lower monoalkyl or N,N-lower dialkylamino, lower thioalkyl, lower alkylsulfonyl or nitro; or 2-furanyl unsubstituted or substituted with at least one of lower alkyl, halo, trifluoromethyl, hydroxy, lower alkoxy, lower acyloxy, amino, N-lower monoalkylamino or N,N-lower dialkylamino, lower thioalkyl, lower alkylsulfonyl or nitro; D and E are hydrogen; Q is hydroxy; and R² and R³ are hydrogen.

4. A compound of claim 3 wherein A is a bond and the sum of n and m is two.

5. A compound of claim 3 wherein A is a bond and the sum of n and m is three.

6. A compound of claim 4 which is N⁶-[(1-phenylcyclopropyl)methyl]adenosine.

7. A compound of claim 4 which is N⁶-[[1-(3-chlorophenyl)cyclopropyl]methyl]adenosine.

8. A compound of claim 4 which is 5'-deoxy-5'-chloro-N⁶-[(1-phenylcyclopropyl)methyl]adenosine.

9. A compound of claim 4 which is N⁶-[[1-(4-chlorophenyl)cyclopropyl]methyl]adenosine.

10. A compound of claim 4 which is N⁶-[(1-thien-2-ylcyclopropyl)methyl]adenosine.

11. A compound of claim 4 which is N⁶-[(1-thien-2-ylcyclopropyl)methyl]adenosine.

12. A compound of claim 5 which is N⁶-[(1-phenylcyclobutyl)methyl]adenosine.

13. A compound of claim 5 which is N⁶-[[1-(3-chlorophenyl)cyclobutyl]methyl]adenosine.

14. A compound of claim 5 which is N⁶-[(1-thien-2-ylcyclobutyl)methyl]adenosine.

15. A compound of claim 5 which is N⁶-[(1-phenylcyclopentyl)methyl]adenosine.

16. A compound of claim 5 which is N⁶-[(1-phenylcyclohexyl)methyl]adenosine.

17. A compound of claim 1 which is N⁶-[(1-phenylcyclopropyl)methyl]adenosine-N¹-oxide.

18. A compound of claim 4 which is N6-(1-(2-chlorophenyl)cyclopropylmethyl)adenosine.

19. A compound of claim 4 which is N6-(1-(2-methylphenyl)cyclopropylmethyl)adenosine.

20. A compound of claim 4 which is N6(1-(2-furanyl)cyclopropylmethyl)adenosine.

21. A compound of claim 4 which is N6-(1-(5-methylthien-2-yl)cyclopropylmethyl)adenosine.

22. A compound of claim 4 which is N6-(1-phenylcyclopropylmethyl)adenosine-5¹-yl hydrogen succinate.

23. A compound of claim 4 which is N6-(1-phenylcyclopropylmethyl)adenosine-5¹-uronamide.

24. A pharmaceutical composition for treating psychosis or hypertension comprising an antipsychotic or antihypertensive effective amount of a compound as claimed in claim 1 together with a pharmaceutically acceptable carrier.

25. A method of treating psychosis in a mammal suffering therefrom which comprises administering to such mammal an antipsychotic amount of a compound of claim 1 in unit dosage form.

26. A method of treating hypertension in a mammal suffering therefrom which comprises administering to such mammal an antihypertensive amount of a compound of claim 1 in unit dosage form.

* * * * *